United States Patent [19]

Cherif Cheikh

[11] Patent Number: 5,542,920
[45] Date of Patent: Aug. 6, 1996

[54] NEEDLE-LESS PARENTERAL INTRODUCTION DEVICE

[75] Inventor: Roland Cherif Cheikh, Issy Les Moulineaux, France

[73] Assignee: Delab, Paris, France

[21] Appl. No.: 304,274

[22] Filed: Sep. 12, 1994

[51] Int. Cl.$^6$ .................................................. A61M 31/00
[52] U.S. Cl. ................ 604/57; 604/59; 604/60; 604/309; 604/311
[58] Field of Search ................ 604/57, 59, 60, 604/64, 309, 310, 311

[56] References Cited

U.S. PATENT DOCUMENTS

| 2,589,388 | 3/1951 | Hunter . | |
|---|---|---|---|
| 2,630,804 | 3/1953 | Mende | 128/238 |
| 3,072,121 | 1/1963 | Feldmann | 128/217 |
| 3,572,335 | 3/1971 | Robinson | 128/217 |
| 4,060,083 | 4/1976 | Hanson . | |
| 4,808,166 | 10/1987 | Davidov . | |
| 4,871,094 | 4/1988 | Gall . | |
| 4,994,028 | 5/1989 | Leonard . | |
| 5,399,162 | 3/1995 | Cselle | 604/60 |
| 5,405,324 | 4/1995 | Wiegerinck | 604/60 |

FOREIGN PATENT DOCUMENTS

| 0292936 | 5/1988 | European Pat. Off. . |
| 698275 | 10/1953 | United Kingdom . |
| 2091554 | 1/1982 | United Kingdom . |

*Primary Examiner*—John D. Yasko
*Assistant Examiner*—Laird J. Knights
*Attorney, Agent, or Firm*—Fish & Richardson P.C.; William E. McGowan

[57] ABSTRACT

A needle-less device for the parenteral administration of a medicament is disclosed. The medicament has the shape of one end of a toothpick. It is placed in the bore of a barrel with the barrel having the shape of a nosecone at one end. A plunger is inserted into the other end of the bore. The plunger forces the medicament through the skin and into the subcutaneous layer of the patient without the need for penetration of the skin by a needle.

13 Claims, 4 Drawing Sheets

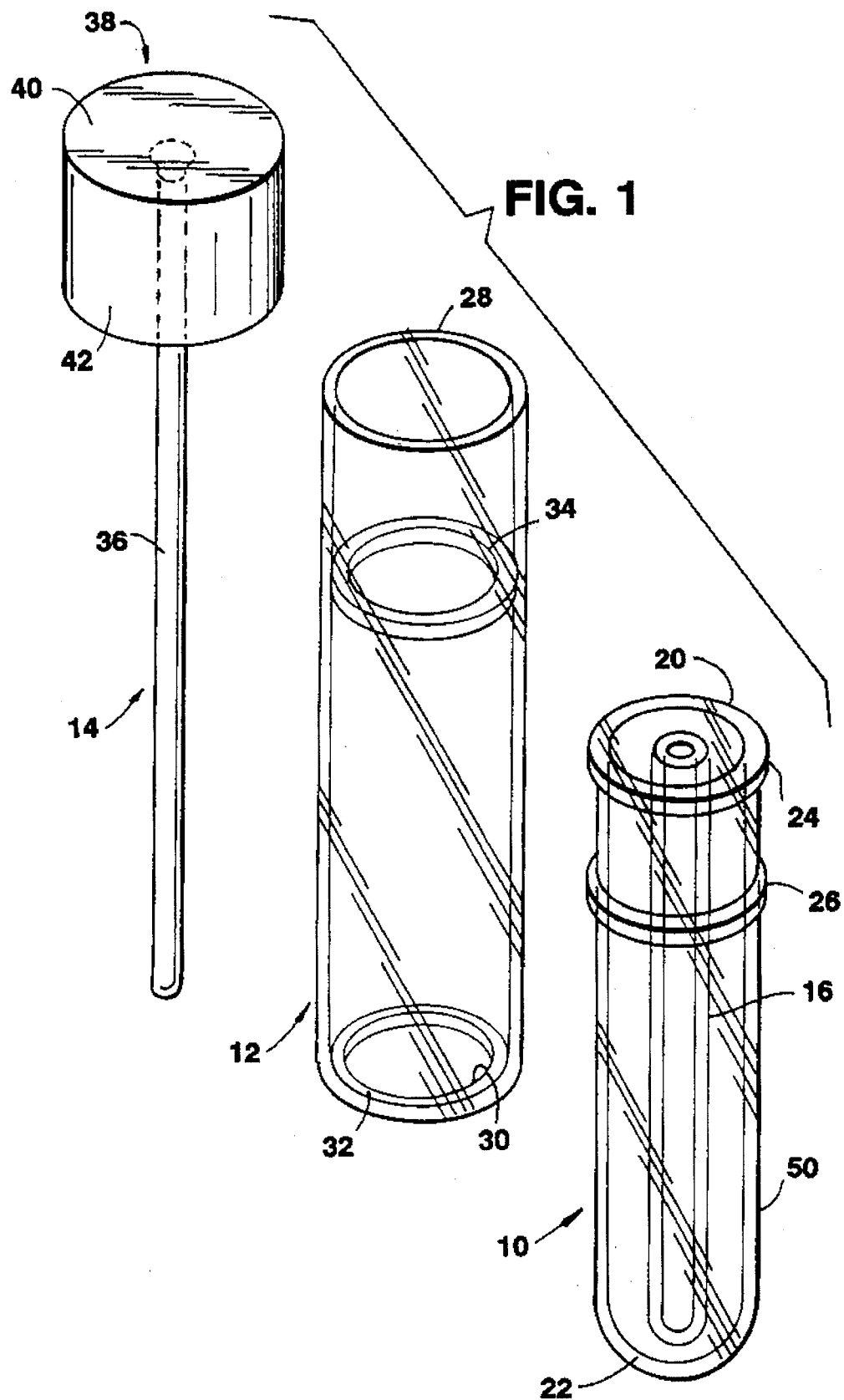

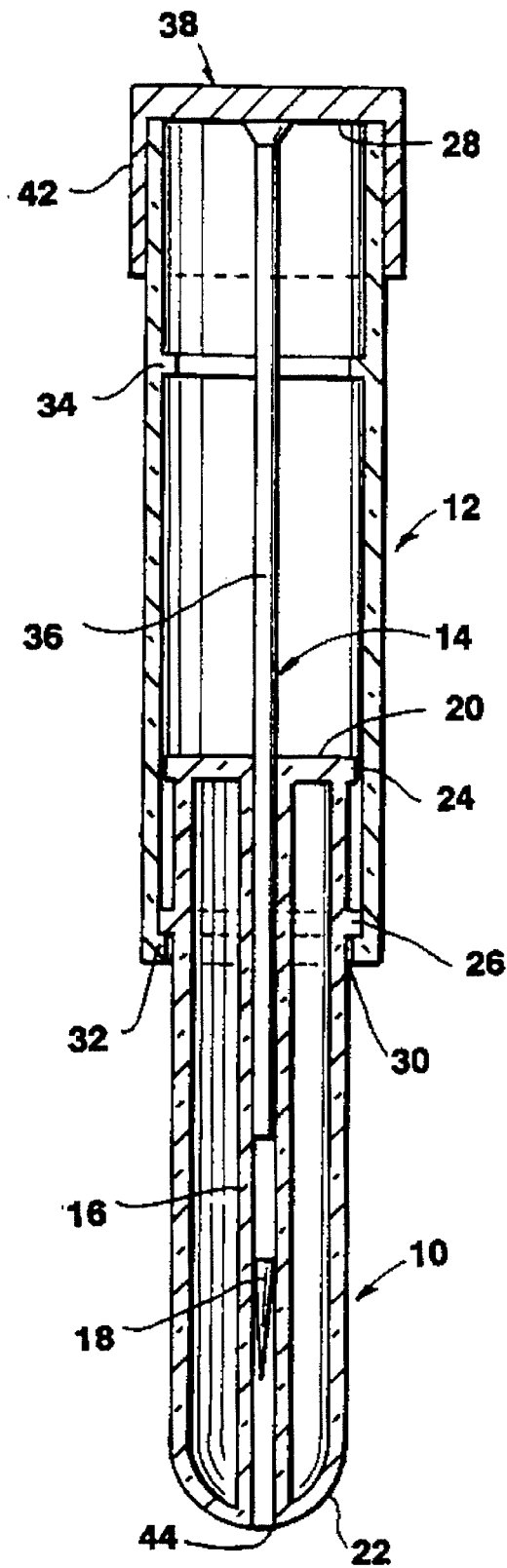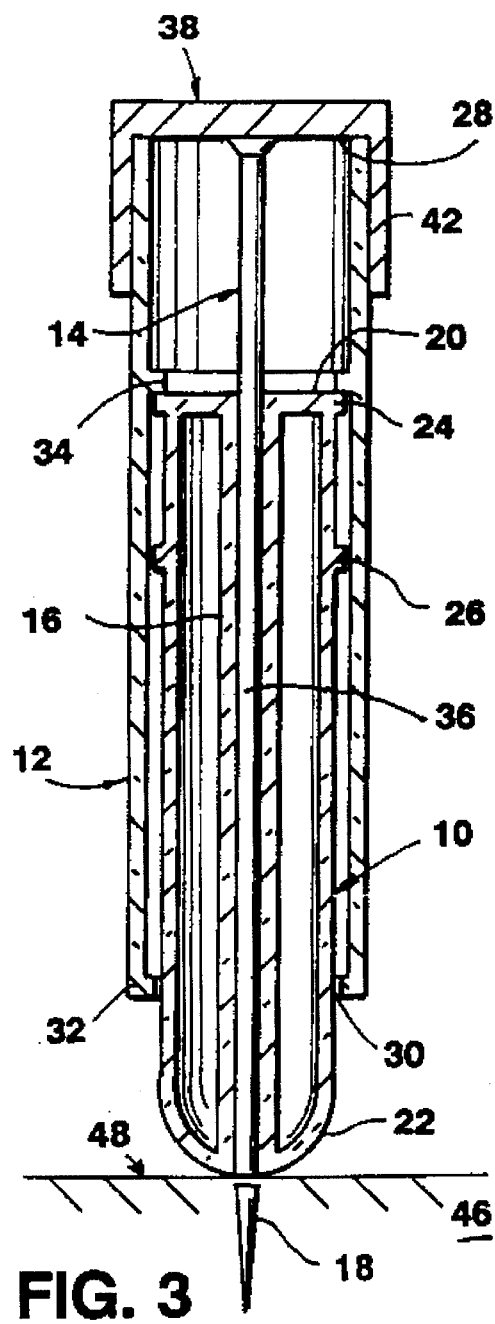
FIG. 2  FIG. 3

NEEDLE-LESS PARENTERAL INTRODUCTION DEVICE

The present invention relates to parenteral introduction devices and, in particular, to a device for intramuscular or subcutaneous administration of a pharmaceutically active composition.

The parenteral route is preferred over oral ones in many occurrences. For example, when the drug to be administered would partially or totally degrade in the gastrointestinal tract, parenteral administration is preferred. Similarly, where there is need for rapid response in emergency cases, parenteral administration is usually preferred over oral.

Thus, while parenteral administration is desirable in many applications, as it is currently practiced, it presents substantial drawbacks. Probably the biggest drawback is the discomfort which it causes the patient to whom the drug is being administered. Parenteral preparations generally contain a large volume of liquid in which the drug is suspended or dissolved. Ratios of active ingredient to carrier commonly run from 1:100 to 1:1000. Especially where the active ingredient is poorly soluble or difficult to suspend, or when it has to be administered at high doses, or in both instances, a fairly large volume of liquid must be injected. The injection of the needle and the introduction of a fairly large volume of liquid cause parenteral administration to be more or less painful, and at least disagreeable, for most people. Furthermore, depending on its nature, the solvent or the suspending agent may itself be a cause of pain.

A further disadvantage to administration of drugs in a liquid carrier is that the drugs are frequently not stable in the liquid. Therefore, the liquid and drug must be mixed substantially contemporaneously with injection. This can be of substantial disadvantage where, for example, many hundreds of people must be treated over a course of days in order to stem an epidemic.

Accordingly, it would be interesting to find a mode of administration avoiding the use both of a needle and of a liquid solution or suspension. As far as the inventor knows, nothing seems to exist in the state of the art.

Parenterally administered solid compositions for use in the controlled release of a medicament are known and devices allowing direct injection of a medicament without need of a liquid are known; for example, trocars for implants of rods or pellets and the device shown in European patent application No. 0292936 A3 for injection of a solid. However, trocars and the device of European Patent Application No. 0292936 A3 still require use of a needle.

The applicant has now discovered a comparatively inexpensive device for the ready administration of solid or semi-solid drugs by the parenteral route. The applicant's device avoids completely the need for a needle. The solid drug is injected directly through the skin by a plunger which enters the skin only to the degree necessary to position the solid drug. The medicament is suitably made in the shape of the end of a toothpick, i.e. it has a pointed end which gradually tapers to a cylindrical portion. The medicament is made of sufficient structural strength so that it can penetrate through the skin into the subcutaneous layer when it is administered with the parenteral introduction device of the present invention. Thus, the drug penetrates the skin and there is no need for the expense of discomfort of a needle to administer the drug parenterally. The present invention also includes an automatic device that can contain a number of doses of medicament which can be administered to a series of patients, one after the other.

These and other aspects of the present invention may be more fully understood from the drawings wherein:

FIG. 1 is an exploded view of the parenteral introduction device according to the present invention;

FIG. 2 shows the parenteral introduction device of the present invention in its retracted form;

FIG. 3 shows the device of the present invention with a medicament having been parenterally introduced into a patient;

Figure 5:
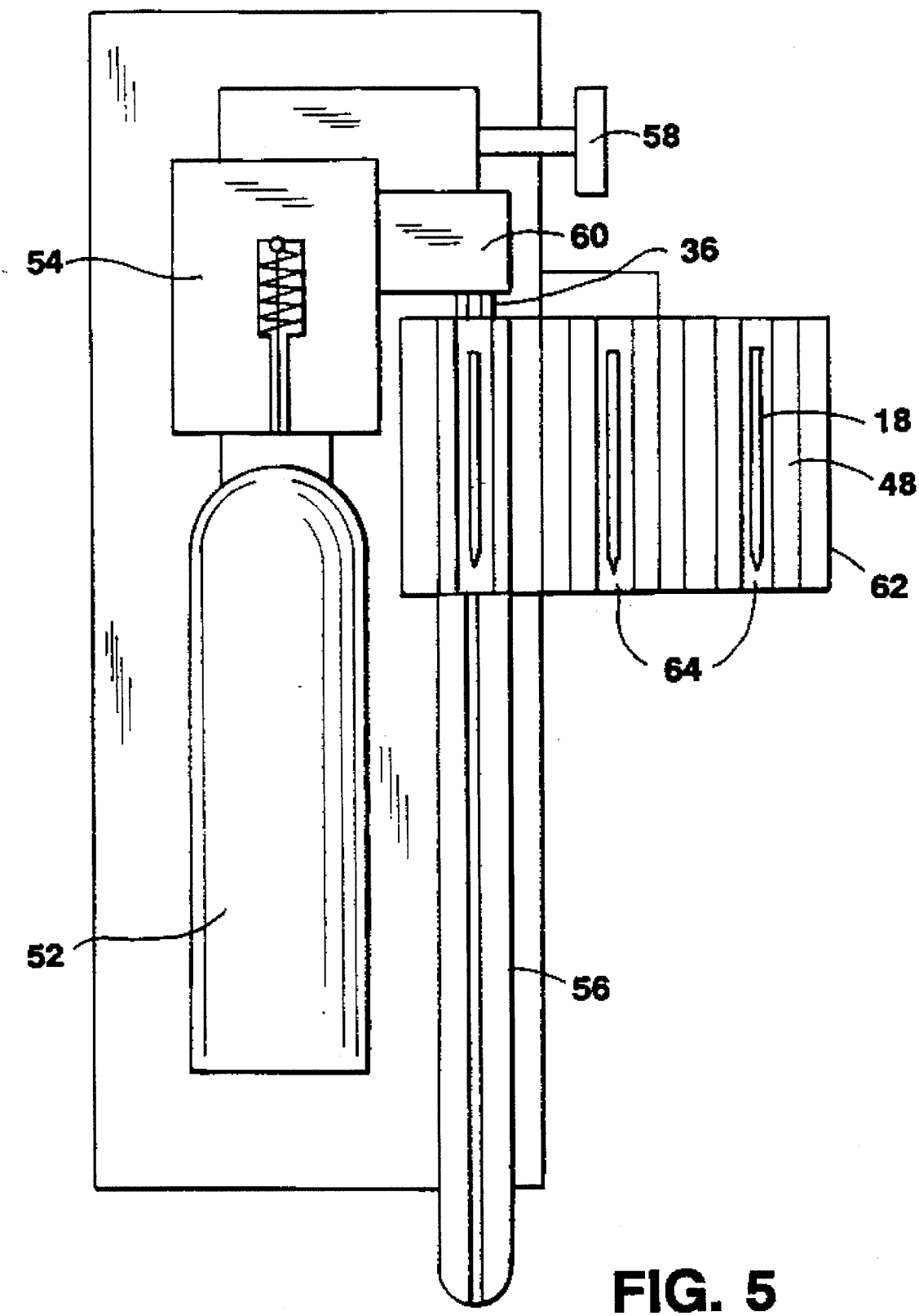
FIG. 5 shows an alternative embodiment of the automatic device for administering seriatim shots to a number of individuals.

Referring first to FIG. 1, which is an exploded view of the parenteral introduction device of the present invention, there are three essential elements, namely a main barrel 10, a sleeve member 12 and a plunger member 14. The main barrel 10 has central bore 16 which extends from one end 22 to the other end 20 of the main barrel 10. A medicament 18 (see FIG. 2) is carried in this central bore 16. The main barrel 10 includes protruding ring members 24 and 26 which act as stops as will be hereinafter discussed. The sleeve member 12 is open at both its top 28 and bottom 30 ends. The sleeve member 12 includes shoulders 32 and 34 to limit travel of the sleeve as hereinafter discussed. Plunger member 14 includes a plunger rod 36 and an end cap 38. The end cap 38 has a circular plate member 40 and a toroidally shaped flange 42. The plunger rod 36 has an external diameter at least a portion of which is substantially the same as, or slightly smaller than, the internal diameter of the bore 16.

FIG. 2 shows the parenteral introduction device of FIG. 1 in assembled condition and in a condition suitable for transport and storage. Plunger member 14 is press fit onto the end 28 of sleeve 12. Sleeve 12 has been forced over main barrel 10 so that shoulder 32 has passed over ring member 24 and has come to rest again ring member 26. The sleeve member is in sliding engagement with the exterior surface of the main barrel 10. Abutment of shoulder 32 with ring member 26 restrains the relative position of the sleeve 12 and the main barrel 10 so that the plunger 14 does not inadvertently dislodge the medicament 18 and push it through the said one end 22 of the main barrel 10. Ring member 24 prevents the unintentional separation of sleeve 12 from main barrel 10 since it will engage shoulder 32 before the sleeve 12 and the main barrel 10 am separated. A seal 44 of a biologically compatible material, such as cellulose or gelatin, may be applied to the end 22 of the main barrel 10 in order to maintain the sterility of the medicament 18 until the time it is administered. Alternatively, or additionally, the entire mechanism can be stored in a sterile environment such as a foil or cellophane pack (not shown).

Turning now to FIG. 3, there is shown the device in use. The said one end 22 of the main barrel 10 has been placed against the skin 48 of the patient to be treated, in such a way as to apply a tension on the zone where the medicament is to be injected. The plunger 14 and the sleeve 12, which travel together, have been urged down the main barrel 10 by applying pressure on the end cap 38 of plunger 14 until shoulder 34 comes into contact with the ring member 24. The plunger rod 36 has traversed the length of the bore 16 of the main barrel 10 and has pushed the medicament 18 through the skin 48 of the patient and into the subcutaneous layer 46. Shoulder 34 of sleeve 12 in combination with ting member 24 of main barrel 10 has limited the extent of travel of the plunger rod 36 in the main barrel 10. It is preferred that the rod 36 of plunger member 14 stop no more than 2 mm below the said one end 22 of the main barrel 10 and it is most preferred that the plunger member not extend at all beyond the said one end 22 of the main barrel 10.

Figure 4:
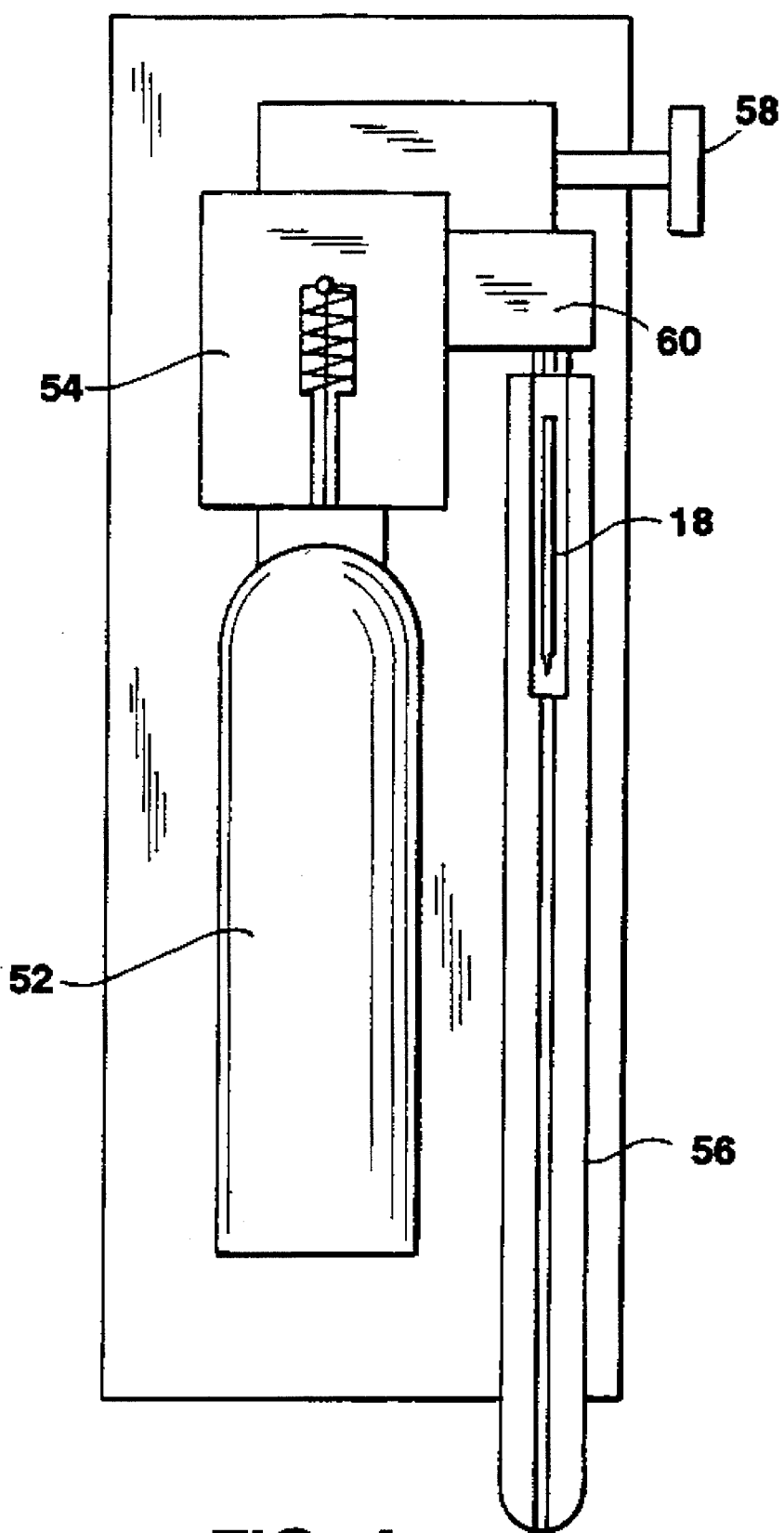
FIG. 4 shows the device of the invention with an automatic system where the plunger is replaced by a means for delivering pressurized gas.

In FIG. 4, there is shown an alternative embodiment of the present invention. In the alternative embodiment, the plunger 14 is replaced by a means for providing gas pressure from a reservoir 52 and through a valve 54. The medicament 18 travels through barrel 56 under pressure of the gas. Barrel 56 can be replaced for each new injection. When an injection is to be made, button 58 is depressed. This allows pressure to flow from reservoir 52 through valve 54 and regulator 60. The gas then forces the medicament 18 through the barrel 56 and into the patient (not shown). In the automatic device, this force is always the same because the amount of pressure exerted on the medicament is controlled by the regulator 60. Thus, the force of the injection is independent of any force applied by the operator.

In FIG. 5, there is disclosed an alternative embodiment of the automatic injector of FIG. 4. In this alternate embodiment, means are provided for injection of a plurality of doses to successive individuals using only a single injection device. This embodiment is illustrated in FIG. 5 where there is a magazine 62 which has a plurality of bores 64 with a medicament 18 fitted into each bore 64. As in the device of FIG. 4, gas pressure forces one of the medicaments 18 into a patient when button 58 is depressed. After delivery of the first medicament, the magazine 62 is moved to the left so that the next adjacent bore 64 and its associated medicament 18 are positioned above the barrel 56. The button 58 can be depressed to create a new gas pressure and to inject this next medicament 18 into the next patient, and, thereafter, the rest of the medicaments 18 can similarly be administered seriatim to a series of individuals. Movement of the magazine can be effected manually or can be done automatically in known manner.

All of the components of the device may suitably be made of plastic material, but it is preferred that the automatic device be made of metal, notably stainless steel. For the manual device, the plunger 36 can be made of metal, but it can also be made of plastic if its cross-section is increased sufficiently. Even where the plunger 36 is made of steel, it may be less expensive to make than the usual syringe since the device of the present invention does not require a stainless steel needle, the making of which requires quite a bit of precision. The main barrel 10 is preferably made with a nosecone shape at end 22.

The main barrel can be made as a single piece, or, alternatively, the space between the outside wall 50 of the main barrel and wall of the central bore 16 can be hollow. The sleeve 12 is preferably made of transparent material so that the plunger rod 36 can be viewed therethrough, thus providing visual assurance that it is in its operative position.

The medicament 18 is preferably made of the shape of one end of a toothpick so that it can easily penetrate the skin and enter the subcutaneous layer. As is well known, one end of a toothpick has a point which tapers back to a cylindrical portion. The medicament is referred to as solid; however, it may be either solid or semi-solid so long as it has sufficient structural integrity to penetrate the skin without breaking apart. It has been found that a medicament having a crush strength of at least about 8 killipoise in the longitudinal direction is sufficiently strong, and lesser crush strengths are also usable, especially for administration to children, who have more tender skin than adults. The amount of carrier in the medicament 18 depends on the drug and on the desired mode of action. As a general rule, the amount of active ingredient in the medicament is at least about 50%. With suitable medicaments which will have sufficient structural strength, the amount of medicament in the present invention can be up to 100%. The medicament may be prepared by conventional techniques such as compression, thermofusion or extrusion. Compression suitably consists of a tabletting process in which a toothpick-shaped microtablet is formed. The size of the medicament 18 may be up to 2 mm in diameter but is preferably from about 0.2 to 0.8 mm, and most preferably from about 0.25 to about 0.5 mm, in diameter for the cylindrical portion of the medicament and about 1 mm to about 3 cm in length. The size will depend, of course, on the dose to be administered and the level of active ingredient present as compared to the amount of carrier. The inside diameter of the bore 16 is preferably about 5-10 % larger than the diameter of the medicament 18. This helps to ensure that the medicament does not get "hung up" or striated by minor imperfections, such as burrs, which may be introduced into the bore 16 during manufacture. At the same time, the diameter is limited to cause frictional engagement so that the medicament is less likely to be inadvertently dislodged from the bore prior to activation of the device. An oil can be added to the bore to increase the tendency of the medicament to remain in the bore; an oil will also assist in penetration through the skin. The diameter of the medicament is not at all arbitrary it has been found that the introduction of a pin with a diameter of about 2 mm or less is substantially painless. Such is not the case for larger diameters, and larger diameter medicaments may generally only be administered via a trocar.

The following are illustrative examples of the parenteral administration of drugs in solid form as compared to the conventional liquid form, and are intended to show that the two means of administration have similar pharmaceutical efficacy.

EXAMPLE 1

A test was conducted with Insulin Human Recombinant (IHR) and Insulin Bovine Pancreas (IBP). IHR is pure water soluble insulin; IBP is zinc insulin, water insoluble and prepared usually using 16% glycerol. IHR and IBP represent about 26 Insulin Units (IU) per mg.

Different doses of insulin were compared with a conventional injectable formulation. In an in vivo test of hypoglycemic effect on rats, all these formulations were found as effective in terms of intensity and rapidity of action.

Insulin can be delivered dry and acts exactly like the usual parenteral formulation for bolus injection. The quantities needed with the device of the present invention are small enough to be administered in solid form as a 2 mm long cylinder with an 0.45 mm diameter. Patients can readily perform virtually painless introduction of solid insulin with the device of the present invention. This form of insulin is also stable for a longer time at room temperature and less expensive than the usual liquid form.

EXAMPLE 2

A formulation of a somatostatine analogue, D-Nat-cyclo [Cys-Tyr-D-Trp-Lys-Val-Cys]-Thr-$NH_2$ was made into injectable tablets by associating the dry material with gelatin and polyvinyl pyrolidone (PVP, 5–10%). The tablets were injected and compared to conventional solutions in terms of pharmacokinetic profiles. The methods gave substantially the same pharmacological results.

EXAMPLE 3

A synthetic anti-PAF, 4,7,8,10-tetrahydro-1-methyl-6-(2-chlorphenyl)-9-( 4-methoxyphenyl-thiocarbamoyl)-pyrido-

[4',3'-4,5]thieno[3,2-f]-1,2,4-triazolo[4,5-a]1,4-diazepine, and a natural anti-PAF, ginkgolide B, were compared to conventional administration. The synthetic anti-PAF cannot conventionally be used parenterally because of its insolubility. Nevertheless, a very good correlation between pharmacological effect and blood concentration has been observed. Ginkgolide B is slightly soluble. For the same dose of product in solution form (pH 8.75), the effect was the same after initial injection but lasted only 2 hours with the solution whereas the effect lasted 24 hours with the dry formulation.

A prolonged formulation of decapeptyl (1 month) was made by molding process with a molding machine into a shape of 0.8 mm diameter and some cm long.

Polylactidecoglycolide (PLGA, 80%) was used. The pharmacokinetically controlled delivery was equivalent to that of an implant or microspheres and the solid form was perfectly injectable subcutaneously or intravenously when the device was used in different species (rabbit, dog, rat and pig).

It will be understood that the claims are intended to cover all changes and modifications of the preferred embodiments of the invention herein chosen for the purpose of illustration which do not constitute a departure from the spirit and scope of the invention.

What is claimed is:

1. A needle-less device capable of parenteral administration of a medicament through the skin without penetration of the skin by said device, said device comprising a barrel member and a plunger, said barrel member having first and second ends and a bore having an inside diameter for receipt of said medicament in solid form, said bore extending from said first end to said second end of said barrel, plunger comprising an elongated rod having an outside diameter, said outside diameter being substantially the same as the inside diameter of said bore, said rod being inserted into the bore at the said second end of said barrel, said plunger being capable of movement in said bore to push said medicament out said first end of the barrel member, through the skin of a patient when said barrel member is pressed against the skin of the patient and when the medicament is of sufficient structural strength to penetrate the skin of the patient, and said first end of the barrel member having a nosecone shape which precludes penetration of the skin by said barrel member.

2. The device of claim 1 further comprising a sleeve, said sleeve being affixed to said plunger and said sleeve being in sliding engagement with the exterior surface of the said barrel member, said sleeve having first and second ends.

3. The device of claim 2 wherein the said barrel includes two spaced protruding ring members, and wherein said first end of the said sleeve has an inwardly extending shoulder, said inwardly extending shoulder retaining said one end of said sleeve in sliding movement on said barrel member between said two ring members on said barrel.

4. The device of claim 2 wherein the plunger comprises a rod affixed to an end cap, said second end of said sleeve being affixed to said end cap.

5. The device of claim 4 wherein the said second end of the sleeve is affixed to the end cap by frictional engagement.

6. The device of claim 3 further comprising a second shoulder extending inwardly from said sleeve, said second shoulder being spaced from said inwardly extending shoulder, said second shoulder in combination with one of the said protruding ring members on the barrel member limiting travel of the plunger rod in the said bore of the barrel member.

7. The device of claim 6 wherein limiting the travel of the said rod is such that no more than about 2 mm of the rod extends beyond the said first end of the barrel member.

8. The device of claim 6 wherein limiting the travel of the said rod is such that none of the rod of the plunger member extends beyond the said first end of the barrel member.

9. The device of claim 1 further comprising a medicament in the bore of the barrel member.

10. The device of claim 9 wherein the medicament has a shape of one end of a toothpick and includes a point with a taper back to a cylindrical portion and wherein said point in said bore is aligned towards the said first end of the barrel member.

11. The device of claim 10 wherein the medicament has a diameter in the cylindrical portion of from about 0.2 to about 2 mm and an overall length of from about 1 mm to about 5 cm.

12. The device of claim 9 further comprising a seal of a biologically compatible material covering the end of said bore located at said first end of said barrel member.

13. The device of claim 12 wherein the biologically compatible material is selected from the group consisting of cellulose and gelatin.

* * * * *

UNITED STATES PATENT AND TRADEMARK OFFICE
CERTIFICATE OF CORRECTION

PATENT NO.   : 5,542,920
DATED        : August 6, 1996
INVENTOR(S)  : Roland Cherif-Cheikh It is certified that error appears in the above-identified patent and that said Letters Patent is hereby corrected as shown below:

Col. 2, line 45, delete "am" and insert therefor -- are --;

Col. 4, line 24, after "arbitrary", insert -- ; --;

Claim 1, col. 5, line 32, after "barrel," insert therefor -- said --.

Signed and Sealed this

Sixteenth Day of December, 1997

Attest:

BRUCE LEHMAN

Attesting Officer

Commissioner of Patents and Trademarks